United States Patent

Lindstrom

[19]

[11] Patent Number: 6,041,271

[45] Date of Patent: Mar. 21, 2000

[54] APPARATUS TO DETERMINE THE OPERATIONAL EFFECTIVENESS OF A MACHINE TOOL AND METHOD THEREFOR

[75] Inventor: Mikko Lindstrom, Streamwood, Ill.

[73] Assignee: Finn-Power International, Inc., Schaumburg, Ill.

[21] Appl. No.: 07/773,319

[22] Filed: Oct. 10, 1991

[51] Int. Cl.[7] .................................................. G06F 19/00
[52] U.S. Cl. .......................... 700/175; 700/179; 700/195
[58] Field of Search ................................ 73/104; 83/552; 700/175, 176, 179, 195; 356/394

[56] References Cited

U.S. PATENT DOCUMENTS

| | | |
|---|---|---|
| 3,636,362 | 1/1972 | Beeman et al. ...................... 356/167 |
| 3,694,637 | 9/1972 | Edwin et al. . |
| 3,841,149 | 10/1974 | Edwin et al. . |
| 3,902,811 | 9/1975 | Altman et al. ...................... 250/559 |
| 4,031,368 | 6/1977 | Colding et al. . |
| 4,176,396 | 11/1979 | Howatt . |
| 4,181,958 | 1/1980 | Juengel et al. ..................... 364/474.37 |
| 4,228,514 | 10/1980 | Weiss . |
| 4,296,474 | 10/1981 | Hurt ................................... 364/474.37 |
| 4,366,543 | 12/1982 | Feller et al. ....................... 364/474.37 |
| 4,382,215 | 5/1983 | Barlow et al. ..................... 364/474.37 |
| 4,412,469 | 11/1983 | Hirota et al. ............................ 83/552 |
| 4,420,685 | 12/1983 | Ohtani et al. . |
| 4,538,493 | 9/1985 | Perazzola et al. ....................... 83/552 |
| 4,620,281 | 10/1986 | Thompson et al. ................ 364/474.18 |
| 4,648,053 | 3/1987 | Fridge ..................................... 356/394 |
| 4,657,396 | 4/1987 | Honda et al. .......................... 356/394 |
| 4,658,688 | 4/1987 | Shak et al. ............................... 83/552 |
| 4,692,690 | 9/1987 | Hara et al. ............................. 356/394 |
| 4,711,579 | 12/1987 | Wilkinson ............................. 356/394 |
| 4,811,253 | 3/1989 | Johns ................................. 364/474.37 |
| 4,854,161 | 8/1989 | Drits ......................................... 73/104 |
| 4,881,177 | 11/1989 | McClean et al. .................. 364/474.37 |
| 4,918,616 | 4/1990 | Yoshimura et al. . |
| 5,048,385 | 9/1991 | Eckett et al. ............................. 83/552 |
| 5,059,905 | 10/1991 | Drits ......................................... 73/104 |
| 5,184,217 | 2/1993 | Doering ................................. 358/106 |
| 5,615,471 | 4/1997 | Perazzolo ................................. 83/552 |

OTHER PUBLICATIONS

"Automatic Detection of Cutting Tool Failure", by Gee et al. presented at session 4C: Cutting Tool Control National Machine Tool Builders' Association 2nd Biennial International Tool Technical Conference, Sep. 5–13, 1984.

*Primary Examiner*—Paul P. Gordon
*Attorney, Agent, or Firm*—Louis Woo

[57] ABSTRACT

To determine whether a machine tool is operating effectively, the present invention system, instead of directly measuring the operating parameters of the machine tool, monitors the presence or absence of any holes made by the machine tool and the quality of those holes, if made. The operational effectiveness of the machine tool is then correlated with the data thus monitored.

35 Claims, 8 Drawing Sheets

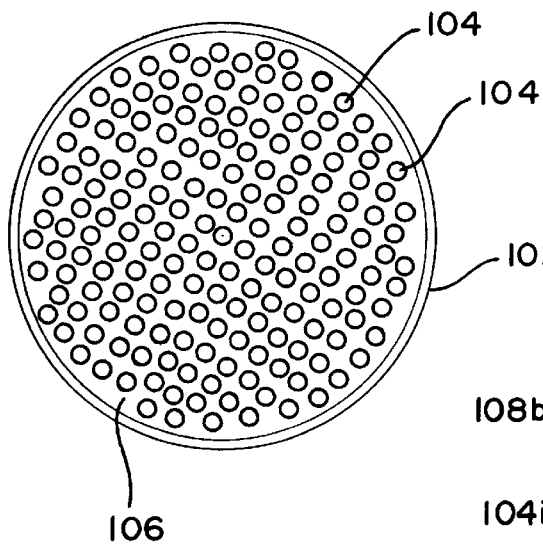
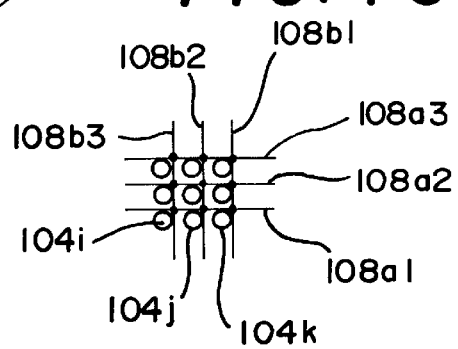
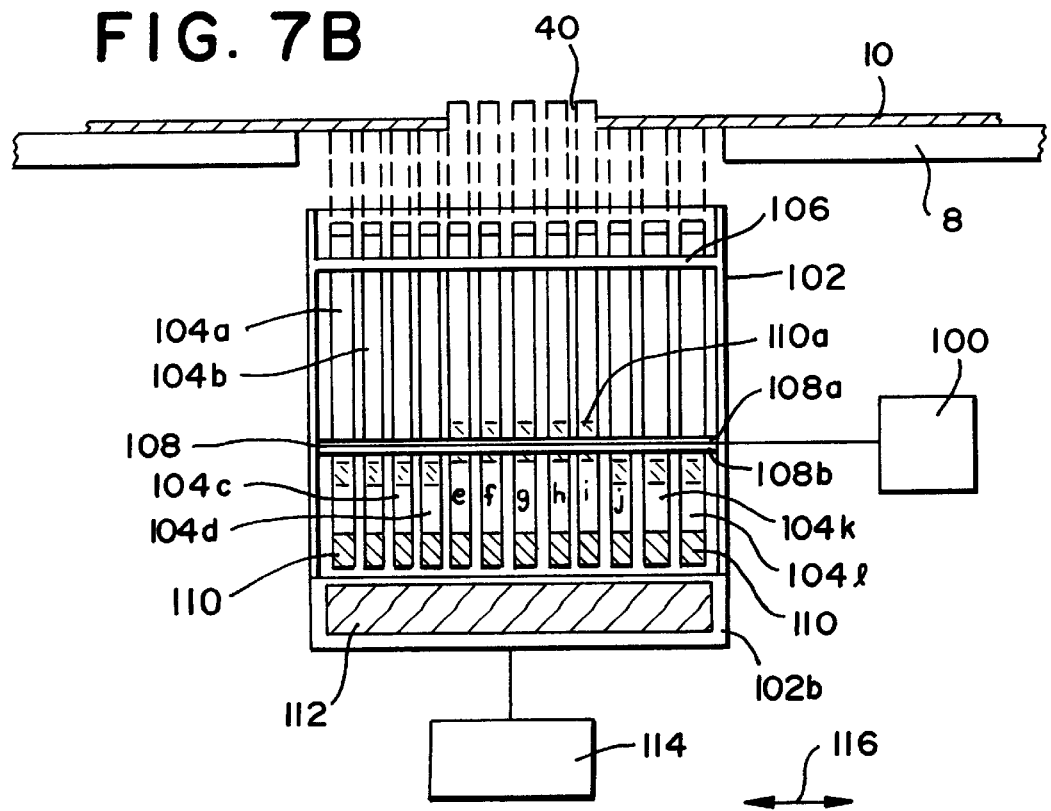

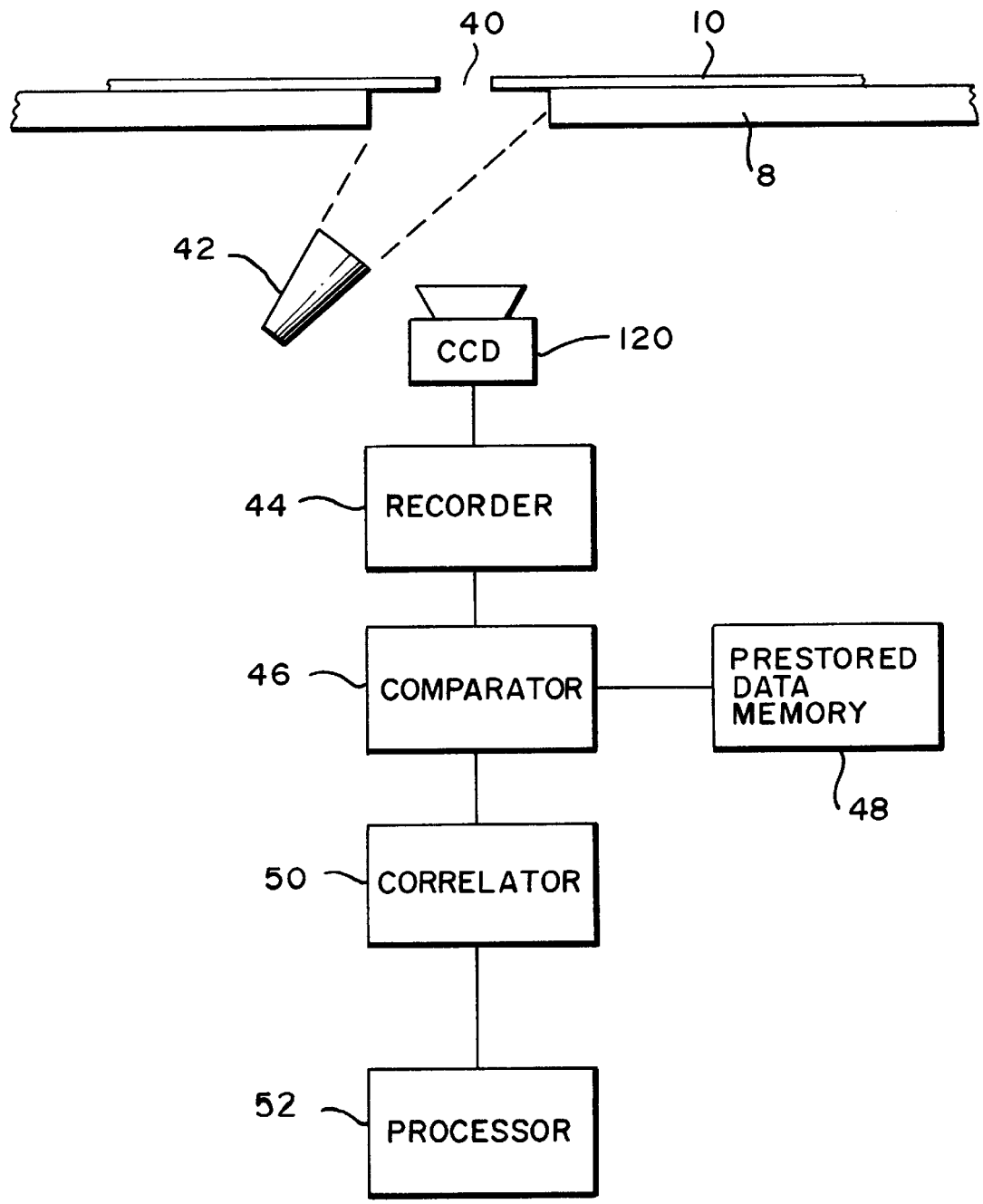

6,041,271

APPARATUS TO DETERMINE THE OPERATIONAL EFFECTIVENESS OF A MACHINE TOOL AND METHOD THEREFOR

FIELD OF THE INVENTION

The present invention is directed to sheet machining centers and more particularly to an apparatus and a method therefor to determine the poerational effectiveness of at least one cutting tool that may be associated with such a sheet machining center.

BRIEF DESCRIPTION OF THE PRIOR ART

The effectiveness with which a machine tool makes a hole or an opening on a workpiece in either a manned or unmanned sheet metal machining center, there are tdwo basic ways in which a punch tool is no longer effective, i.e. breaks down. The first is when the tool has been used a large number of times such that its cutting portion becomes progressively duller until eventually it no longer cuts. The other way is when a tool "slivers", which means that the tool is poerationally ineffective, i.e. broken or partially broken, and that the openings produced by the tool are of poor quality.

To elaborate, if amachine tool for making holes on a workpiece is broken or partially broken, the machine tool, when it is driven to cut a hole in a worksheet, would tend to "stick" to the worksheet so that, when it retracts, the worksheet is pulled thereby. Accordingly, a worksheet could be pulled out of the clamps that are holding it. And if an operator or bystander is nearby, such unanticipated withdrawl of the worksheet could become a safety hazard and possibly cause great harm to such person.

Another problem arises when an operator fails to notice that a machine tool no longer makes holes on a worksheet. As a result, that unpunched worksheet is passed along the production line for further processing. Of course, without the needed holes, parts formed from that worksheet are useless. Consequently, additional manufacturing costs are incurred.

Yet a further problem occurs when the sheet manufacturing machine is a part of an automatic machining center where unmanned production takes place. In those instances where there is no human intervention, chances are even greater that worksheets having missing holes and/or poor quality holes (i.e. holes that are not cleanly cut and have, for example, slivers attached to the edges of the holes) will be amplified, thereby causing greater delay in deliveries and lost profits.

There are disclosed in the prior art various systems and methods of detecting tool failures. For example, U.S. Pat. No. 4,420,685 discloses a system whereby a broken tool is detected by measuring the quantity of collected chips or particles resulting from the machining of a workpiece. U.S. Pat. No. 4,918,616 discloses another system whereby a signal generating unit is mounted near the machine tool for generating a signal towards the machine tool. An acoustic emission transducer, also mounted near the machine tool, is driven by the signal from the signal generator so as to apply an artificial signal to the machine tool. An acoustic signal generated from the machine tool in response to the artificial signal is then sensed and analyzed to determine if there is machine tool failure.

U.S. Pat. No. 4,228,514 discloses a tool wear system for determining the wear of a drill bit by means of its rotational speed. U.S. Pat. No. 4,176,396 discloses yet another tool wear detection system which utilizes a sensor for producing an output signal that is representative of the cutting profile of the tool. Information relating to the cutting profile is stored in a data processing system when the tool was initially installed. Such information is then compared with updated cutting profile information to provide wear characteristics of the tool.

Yet another tool wear detector system is disclosed in U.S. Pat. No. 3,841,149. There a reference value representing the broadband vibrational energy output from the tool in a relatively unworn condition is compared with the vibrational energy levels during successive and regular tool utilization intervals so that updated wear condition of the tool can be determined. U.S. Pat. No. 3,694,637 also discloses a system for monitoring tool wear whereby Fourier analysis is used to transform a vibrational characteristic of the tool into a power frequency distribution to be compared with a reference spectrum obtained from a test tool. The analysis of the different spectra of the '637 patent is performed by a minicomputer while the vibrational characteristics from the machine tool drill is obtained by an accelerometer.

U.S. Pat. No. 4,031,368 discloses yet another system of determining the wear of a machine tool. In particular, the '368 system utilizes different measured quantities such as the face wear, flank wear, and minor flank wear of the cutting tool, the dimension of the machined workpiece, its vibration, deflection and surface roughness etc. to calculate, via a controller, the predicted tool life of the machine tool. In the article entitled "Automatic Detection of Cutting Tool Failure" by Gee, et al., three available methods of tool failure detection are discussed. They are: acoustic emission monitoring, cutting force measurement and power measurement.

In the prior art, therefore, to detect a machine tool failure, the focus has mostly been directed to the machine tool per se. Thus, substantially all of the prior art has to take into account the movement of the machine tools which oftentimes entail designing elaborate circuities for overcoming the vibrations and movement of the tools. Moreover, the need to monitor a machine tool directly dictates the need to have a monitoring mechanism located adjacent to the machine tool. Such proximate location of a monitoring mechanism to a moving machine tool is quite often a difficult, if not impossible, task. Furthermore, to detect tool wear in a hydraulic punching machine, in using the above noted methods, hydraulic pressure sensitive mechanisms are needed. However, there are in operation myriad mechanically operated machines where hydraulic pressure sensors are not adaptable to.

BRIEF DESCRIPTION OF PRESENT INVENTION

The inventor has found that the safest and surest way of detecting a broken tool is to qualify the hole (or opening) made by the tool. Putting it simply, the inventor realizes the following three possible scenarios when a machine tool attempts to make a hole or an opening in a worksheet: (a) no hole or opening; (b) a damaged hole or opening; and (c) a perfect hole or opening. In the case where a perfect hole was made, obviously no action is required on the part of the operator of the system. However, such is not the case for (a) and (b) where there is either a hole missing or a poor quality hole made.

Thus, the inventor recognizes that by "looking at the hole", at any time during the operation of the machine work cycle, the effectiveness of a tool can be determined. Such "look at the hole" method in effect provides great flexibility to the system since it can be effected remotely from where the actual physical punching or cutting of a hole takes place. Moreover, by being able to locate an apparatus remote from where the punching or cutting takes place, i.e. remote from the machine tool, many different types of apparatus for determining the quality of the holes which are more reliable and less expensive than prior art systems can be utilized.

In particular, the inventor envisions a number of apparatus and methods therefor of effecting a system for qualifying a hole, if made, on a worksheet by a machine tool and correlating the quality of such hole to the operational effectiveness of the machine tool. For example, a photoelectric mechanism using a sensor for detecting holes made by a machine tool can be used. Another practical example mechanism envisioned by the inventor includes the use of a camera for recording an image of the hole and comparing it with a prestored image of a hole made by a new machine tool, i.e. a perfect or desired hole. Yet another mechanism envisioned by the inventor involves the use of a mechanical probe or a plurality of probing elements for physically measuring the presence of a hole and the quality of such. To define the quality of a hole, a movable probe that records the coordinates it touches is also envisioned.

Irrespective of whichever mechanism is used, by locating the mechanism for detecting any holes made by a machine tool on a worksheet close to but not in contact with the machine tool, the detection of any effected holes may take place at the same time that the worksheet is being maneuvered on the worktable during the production run. Such coexistent production and detection minimize, if not totally eliminate, any lost production time due to hole detection.

It is therefore an objective of the present invention to provide a system for measuring the operational effectiveness of a machine tool.

It is another objective of the present invention to provide a system that can detect the presence of a broken tool.

It is yet another objective of the present invention to provide a system and method for monitoring the operational effectiveness of a machine tool without needing to pay particular attention to the movement, vibration, deflection etc. of the machine tool.

BRIEF DESCRIPTION OF THE FIGURES

The above-mentioned objectives and advantages of the present invention will become more apparent and the invention itself will be best understood by reference to the following description of embodiments of the invention taken in conjunction with the accompanying drawings wherein:

FIG. 7A is a plan view of yet another embodiment detection mechanism of the present invention;

FIG. 7B is a side view of the FIG. 7A detection mechanism;

FIG. 7C is a partial plan view of the magnetically conductive layers of the FIG. 7B detection mechanism;

FIG. 8 is a simplified schematic block diagram of yet another system of the present invention.

DETAILED DESCRIPTION OF EMBODIMENTS OF THE PRESENT INVENTION

Figure 1:
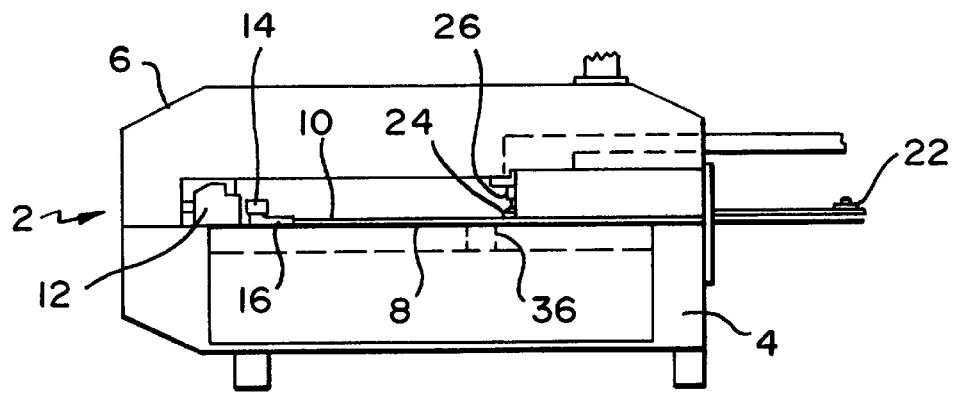
FIG. 1 is a side view of a representative sheet metal machining station to which the present invention is applicable.
Figure 2:
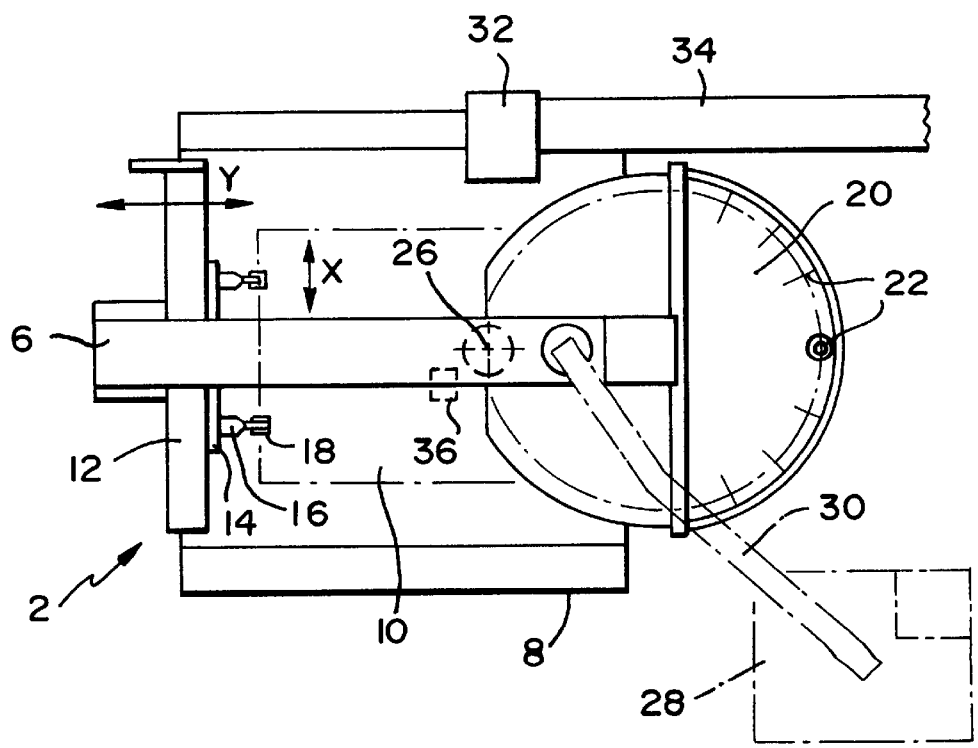
FIG. 2 is a plan view of the FIG. 1 machining station.

With reference to FIGS. 1 and 2, an automatic sheet metal machining center to which the system of the instant invention can be applied is shown in side view (FIG. 1) and plan view (FIG. 2). Albeit a sheet metal machining center is shown, it should be noted that the system of the present invention is equally applicable to stand alone machines such as punchers, laser cutters and plasma cutters. Furthermore, although shown to operate with turret punch and laser cutter machine tools, the machining center of FIGS. 1 and 2, as is well known, can also contain machine tools such as a plasma cutter.

As shown, automatic sheet metal machining center 2 has a base frame 4 to which a top frame 6 is mounted. A worktable is indicated at 8 upon which a worksheet 10 is placed. For the illustrated automatic sheet metal machining center, movably mounted to frame 4 is a first carriage 12 which is movable along the directions indicated by the Y arrows. Movably mounted to carriage 12 is a second carriage 14 which is movable along first carriage 12 in the directions as indicated by the X arrows. Two grippers 16 are shown to be connected to second carriage 14. As taught in U.S. Pat. No. 4,658,682, the disclosure of which being incorporated herein by reference, each gripper 16 has a pair of jaws 18 for grasping worksheet 10.

Also rotatably mounted to top frame 6 is a turret 20 to which a number of tools, of which tools 22 and 24 are shown in FIGS. 1 and 2, are movably fitted. As is well known, turret 20 is rotatable along a center axis (CT in FIG. 4) such that each of the tools movably fitted near the periphery thereof can be positioned under a puncher at a location 26 for effecting a hole, or an opening, on worksheet 10. As can be gleaned from FIG. 2, inasmuch as first carriage 12 is movable along the Y axis and second carriage 14 along the X axis, worksheet 10 can be moved anywhere on table 8 via a combination of movements by carriages 12 and 14. Thus, a selected portion of worksheet 10 can be moved to location 26 under tool 24 so that the puncher can strike tool 24 for effecting a hole on worksheet 10.

As is well known and shown in FIG. 2, the operation of sheet metal machining center 2 is controlled by a computerized numerical controller (CNC) 28, connected to machining center 2 by cables through a conduit 30.

In addition to being able to punch a hole on worksheet 10 by the puncher at location 26, holes or openings on worksheet 10 can also be effected by a laser cutter (or plasma cutter) whose cutting head is shown at 32. The laser beam pathway which leads cutting head 32 to the laser generator (not shown) is designated 34. Insofar as such laser cutter is well known and is disclosed, for example in U.S. Pat. No. Re 31,042, further discussion of the same is not deemed necessary. Suffice it to say that laser cutter head 32 effects cutting on worksheet 10 by a combination of laser energy and oxygenated fluid.

Further, as was mentioned above, a laser cutter does not need to work in conjunction with a turret punch press, as it may in actuality be a stand alone machine. So, too, the present invention is not limited to just a laser cutter, turret punch press or plasma cutter, as it is equally applicable to any machine tool that is capable of effecting an opening onto a worksheet. However, for the FIG. 2 machining center illustration, holes may be made onto worksheet 10 by both the turret punch press and laser cutter.

Figure 3:
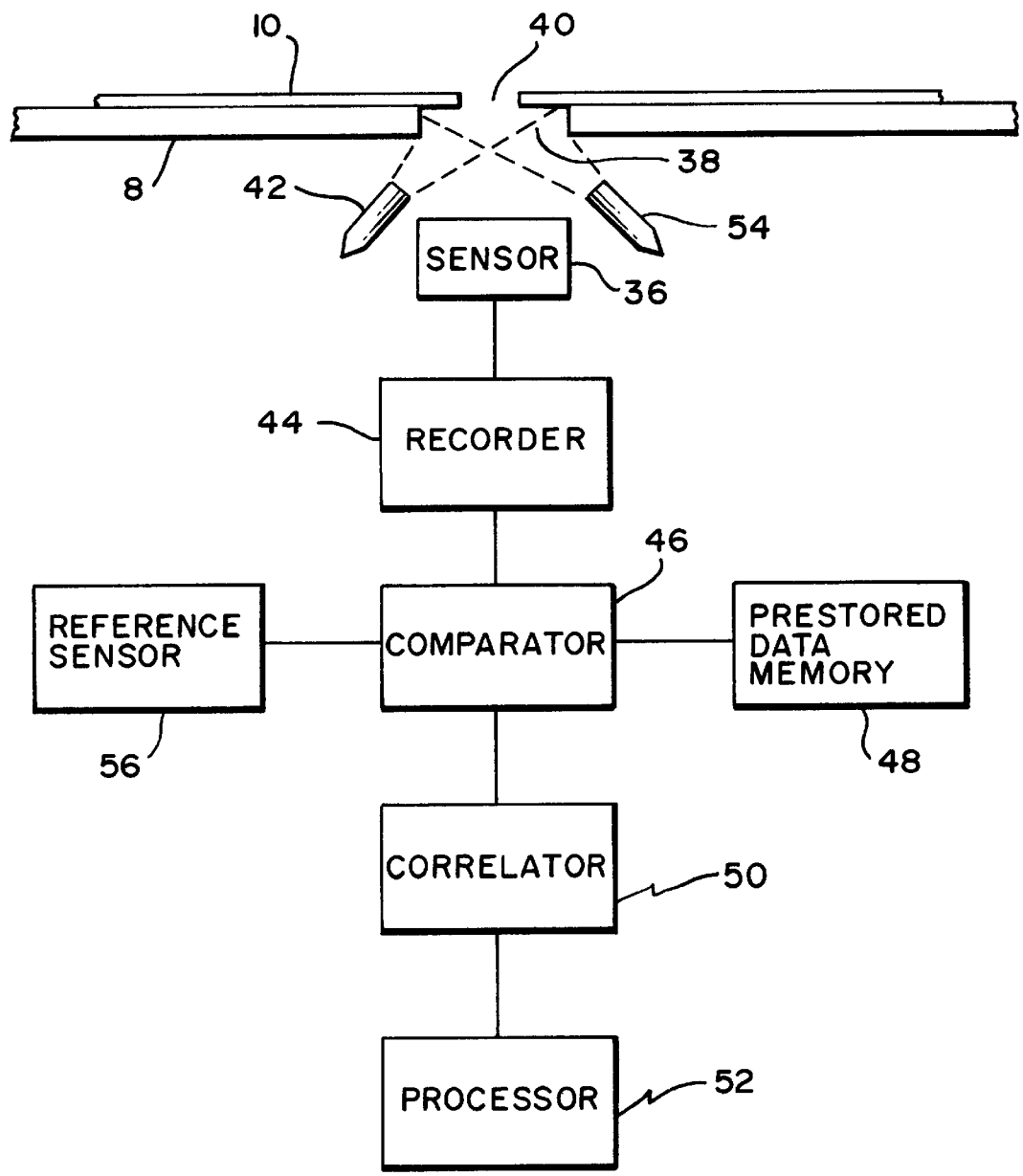
FIG. 3 is a simplified block schematic of an exemplar system of the present invention.

With reference to FIG. 3, a simplified combination of a block schematic and a side view of a worksheet resting on a worktable is shown. The worksheet and the worktable, being the same as those shown in FIGS. 1 and 2, are accordingly numbered the same.

As shown, a conventional sensor 36 is placed just beneath an opening 38 of worktable 8. Thus, as workpiece 10, more specifically, the selected portion thereof which contains an effected hole 40 is placed above sensor 36, it is sensed thereby. Sensor 36 may be any conventional sensor.

For the FIG. 3 system, to enhance sensing by sensor 36, an electromagnetic wave emitting means such as a light source 42 may be placed proximate to opening 38 to illuminate the surroundings thereof. There are myriad ways in which sensor 36 may be used to sense opening 40 of worksheet 10. One of which is the collective sensing of the light passing through hole 40 as an image. Another is the sensing of the echo of the electromagnetic wave from source 42 reflected from the surrounding areas of opening 40 as an image. Such images are fed by sensor 36 to a recorder 44. Each of the thus recorded images is forwarded to a comparator 46 where it is compared with prestored data representing, for example, an image of a desired, or optimal, hole from a prestored data memory 48.

The result obtained from the comparison between the sensed image and the prestored image is next forwarded to a correlator 50 for correlation with the operational effectiveness of the machine tool which had effected hole 40 on worksheet 10. The operation of correlator 50, not to mention that of recorder 44 and comparator 46, is controlled by processor 52, which in the case of the sheet metal machining center shown in FIGS. 1 and 2, could be CNC 28. The method in which hole 40 is discriminated by sensor 36 and compared with the prestored data from memory 48 is conventional and can be referenced to in U.S. Pat. No. 5,020,114 in which a two-dimensional image from an imaging unit is obtained by subtracting a background image prestored in a memory. The '114 disclosure is incorporated to the disclosure of the present invention by reference herein.

Instead of just obtaining an image of hole 40 and directly comparing the same with prestored data, a second optional emitting source 54, shown positioned adjacent to opening 38 of worktable 8, may be added to the FIG. 3 system. With the optional emitting source, an electromagnetic wave which has a frequency different from that emitted from source 42 may be emitted towards hole 40. Insofar as the frequencies of the electromagnetic wave from light source 42 and that from source 54 are different, with the appropriate conventional sensor 36, the different electromagnetic waves are substracted from each other. And with the different electromagnetic waves being emitted at different angles, an accurate measurement of hole 40 can be obtained. A method whereby two different electromagnetic waves may be combined for obtaining an accurate image is taught in U.S. Pat. No. 3,636,362, the disclosure of which is incorporated by reference herein. The mathematics used for correlating the area of a hole obtained from the collection of an electromagnetic wave, i.e. light, is taught in U.S. Pat. No. 3,806,252, the disclosure of which is likewise incorporated by reference herein. Such methods could of course be used in correlator 50' for correlating the measured image against some prestored data to ascertain the operational effectiveness of a machine tool.

For the FIG. 3 system, to enhance the image collected by sensor 36, a reference sensor such as 56 could be used. The purpose of reference sensor 56 is to compensate for any ambient light that may otherwise affect the sensed image. For example, a sensed image of hole 40 could be affected by ambient light. Thus, by compensating for the ambient light by subtracting the same from the reference light sensed by reference sensor 56, an enhanced image of hole 40 is obtained.

Figure 4:
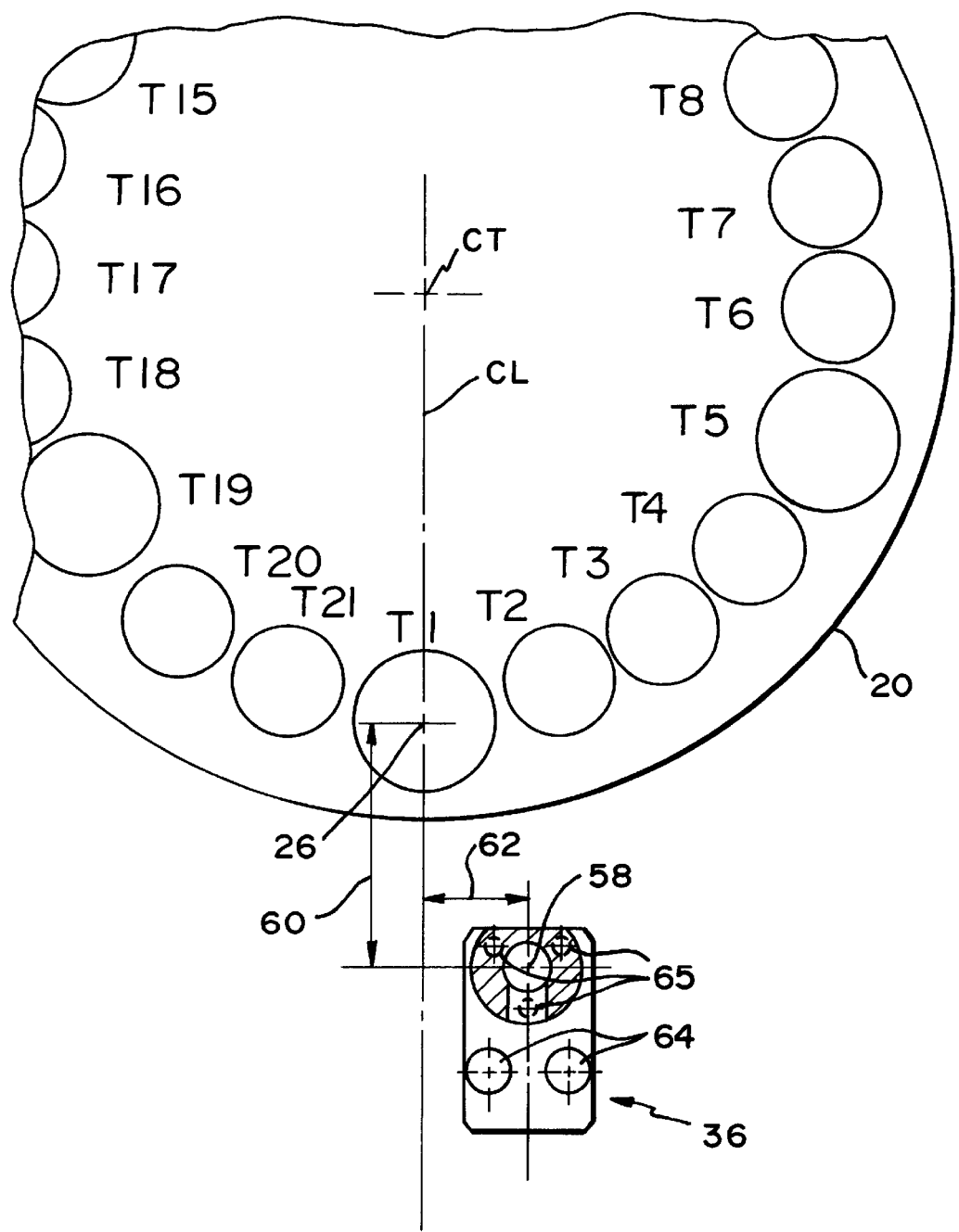
FIG. 4 is a plan view of a turret and the relative location of a first embodiment mechanism detector for the present invention.
Figure 5:
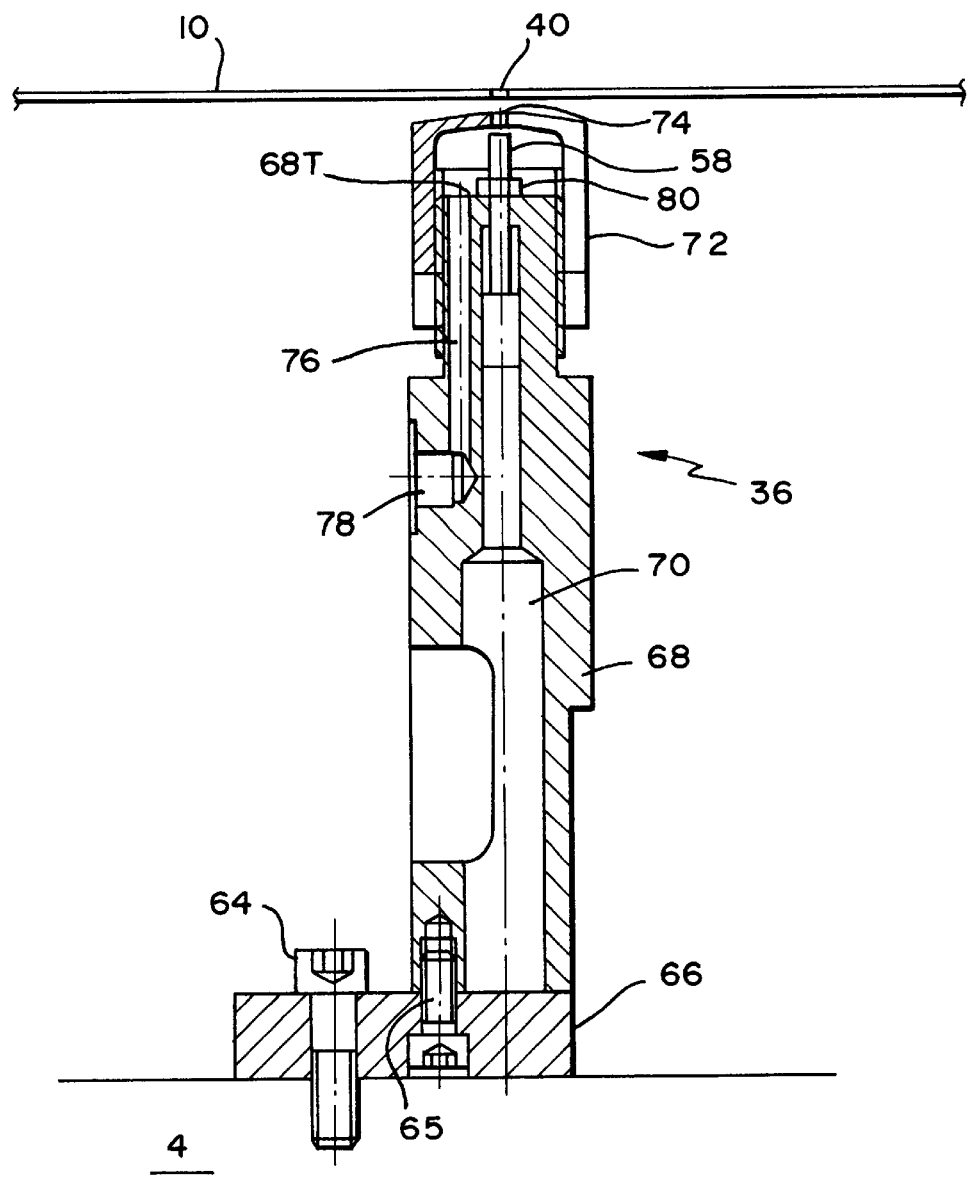
FIG. 5 is a side view of the first embodiment mechanism of the present invention.

A specific embodiment of sensor 36 is shown in FIGS. 4 and 5. With reference to FIG. 4, there is shown the placement of a first embodiment detector with reference to turret 20 of the sheet metal machining center of FIG. 2. With regard to turret 20, it should be noted that there are mounted at the periphery thereof a number of tool stations T1 to T20, each containing at least one tool for effecting a hole on worksheet 10. The rotation center of turret of 20 is designated CT and the center line of turret 20 is designated CL.

As is well known and alluded to above, to effect a particular opening on a worksheet, assuming a selected portion of the worksheet has been positioned between the turret and the worktable at location 26, turret 20 is rotated until the tool for making the particular opening is positioned at location 26. Thereafter punch 26 (FIG. 1) comes down to drive the tool against the worksheet to effect the particular opening thereon. For the sake of clarity, worksheet 10 is not shown in FIG. 4. Sensor 36, or rather an actual detector 58, is offset from punch location 26 by Y axis direction distance 60 and from center line CL of turret 20 by X axis direction distance 62. The location of sensor 36 with reference to turret 20 can also be gleaned from FIGS. 1 and 2.

As shown in FIGS. 4 and 5, sensor 36 is attached to a portion of base frame 4 by its base 66 via bolts 64. Extending from sensor base 66 is a housing 68 the hollow top portion of which is fitted with detector 58, which is made by the Telemecanique Company of Westminster, Md. Housing 68 is fixed to base 66 by bolts 65. Although not shown, the wiring for detector 56 in actuality extends into cavity 70 of housing 68. To protect detector 58 from dirt, debris and fallouts from any cutting operation, a cap 72 is threadedly mated to the top portion of housing 68.

As shown, cap 72 has an opening 74 through which detector 58 senses light passing through hole 40 of worksheet 10. To ensure that opening 74 is not blocked by dirt or slivers from the cut worksheets, an air passage 76 is provided from tip 68T of housing 68 to an input valve opening 78 at the mid-section of housing 68. With the appropriate air connection (not shown), air can be blown into valve opening 48, and along air passage 76, to force any dirt or debris out of opening 74.

Also to be noted with respect to detector 58 is the way it is mounted to housing 68 by threaded nut 80. By adjusting nut 80, the height of detector 58 can be adjusted to be either closer to or further away from hole 40 of worksheet 10. Likewise, cap 72 is also threadedly adjustable to accommodate any adjustment of detector 58. The respective sizes of detector 58 and opening 74 are of course dependent on the envisioned size of hole 40. For example, if hole 40 is to made by a punch having a ⅜" diameter, then naturally detector 58 and opening 74 are configured accordingly so as to be able to sense the entire ⅜" opening of hole 40.

Referring back to FIG. 4, inasmuch as the location of sensor 36 is remote from punch area 26—due to its X and Y offsets, any debris caused by the punching operation would not fall onto it. And insofar as sensor 36 is in essence isolated from the punching operation, since it is not in contact with worksheet 10 or worktable 8, it is not affected by any vibration, deflection or movement of either worktable 8 or worksheet 10. Furthermore, since sensor 36 is located only a short distance from punch location 26, for an automatic sheet metal machining center such as that shown in FIG. 2, worksheet 10 needs only to be moved a short distance, i.e. location 26 to detector 74 across the distances indicated by 60 and 62, for detection.

Accordingly, for the system of the present invention, worksheet 10 can actually be operated on by the machine tool while a previously made hole, if any, and the quality of that previously made hole are sensed by detector 58 and defined accordingly. As noted previously, the quality, i.e. the definition of the hole, can be directly obtained from detector 58.

Figure 6A:
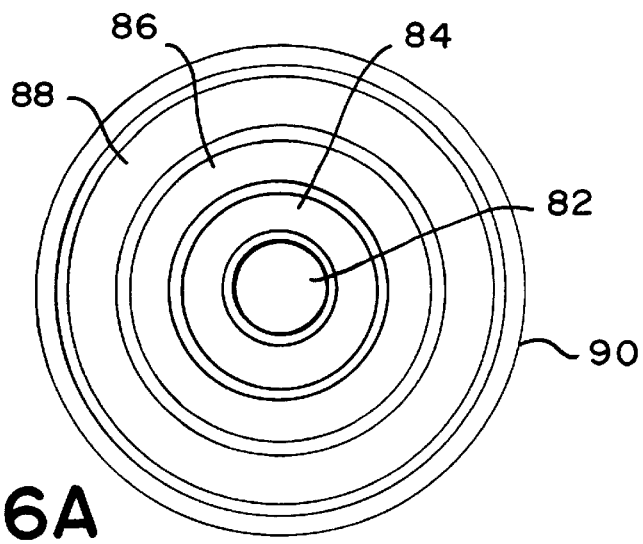
FIG. 6A is the plan view of a second embodiment detection mechanism of the present invention.
Figure 6B:
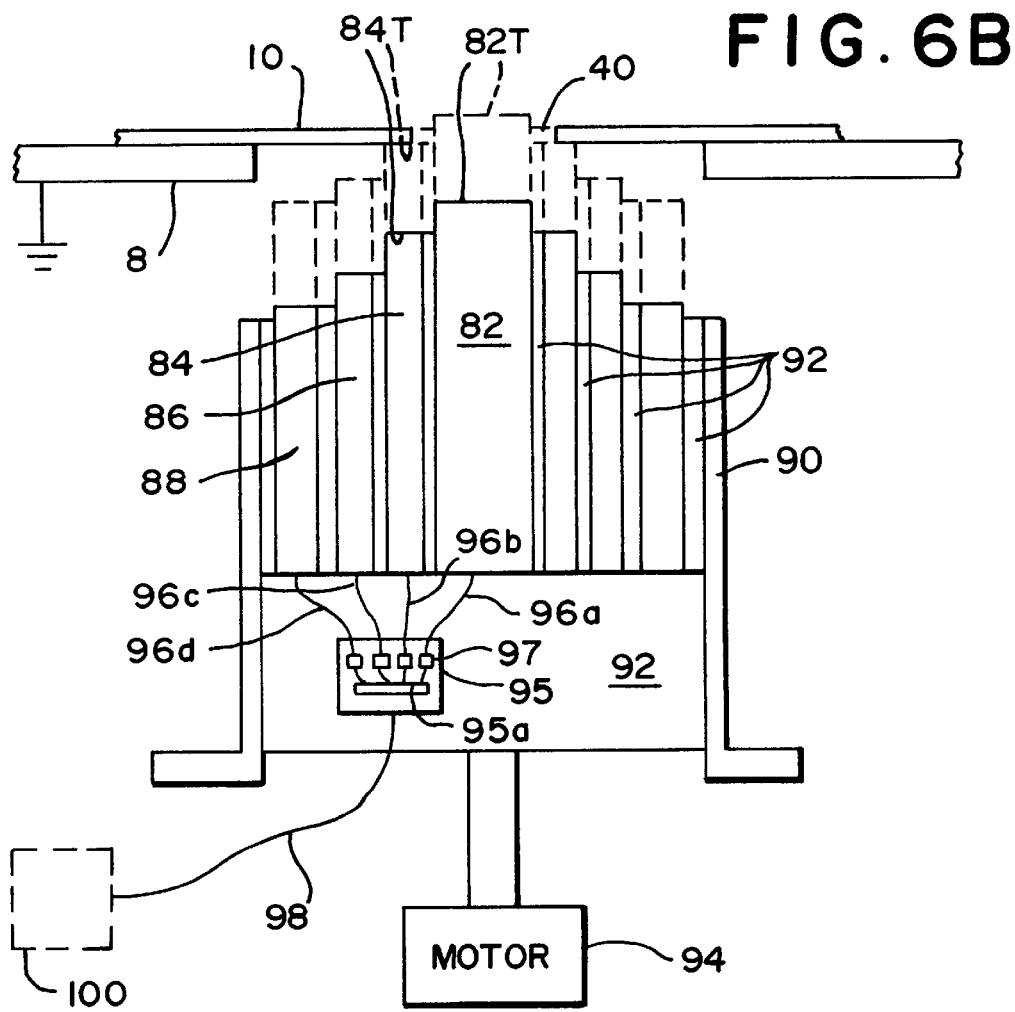
FIG. 6B is a side view of the FIG. 6A embodiment mecanism.

A mechanical embodiment equivalent of sensor 36 is shown in FIGS. 6A and 6B. The mechanism shown in FIG. 6A and 6B comprises a plurality of concentric progressively smaller elongated elements 84–88 surrounding a center probe element 82. The elements are provided within a housing 90 which may be attached to frame portion 4 by bolts (not shown). The different elongated elements are insulated from each other, either by space or by an insulating material designated 92. The elements are in turn fixed to a base 92, which may be driven longitudinally along the length of housing 90 by a driving mechanism 94. Residing in base 92, but which may also be residing elsewhere, is a sensing mechanism 95, which for example may include a potentiometer 95a to indicate the activation of the different ones of the elements 82–88. Potentiometer 95a has different portions thereof connected, via switches 97, by leads 96a–96d to elements 82–88, respectively. In place of a potentiometer, conventional different position indicating switches may also be used. Sensor mechanism 95 is connected by a lead 98 to a definition recorder 100. The definition recorder could of course be the same as recorder 44 shown in FIG. 3.

The sensor mechanism of FIGS. 6A and 6B operates as follows. Once worksheet 10 has been worked on, presumably having a hole made thereon by either a tool punch, a laser or plasma cutter, it is moved (either manually or by grippers when being machined in an automatic machining center) so that the selected portion where the hole should be is positioned above the FIG. 6A and 6B mechanism. As shown in FIG. 6B, once the worksheet has been so properly positioned, motor 94 is energized to drive the different elongated elements 82–88 upward towards worksheet 10. If there is no hole, then of course tip 82T of element 82 could not go past the plane where worksheet 10 lies. If there is indeed a hole, as for example hole 40 shown in FIG. 6B, then tip 82t of element 82 would pass into, and beyond, the plane of worksheet 10. This is indicated by the dotted line designated tip 82T. However, at the same time, assuming that hole 40 is of a size which is only slightly larger than the diameter of element 82, tip 84T of element 84 would come into contact with the lower face of worksheet 10. At that time since worktable 8 is grounded and worksheet 10 is in contact therewith, provided that elongated element 84 is made of a conductive material, a signal is provided through lead 96b to sensing mechanism 95, be it a potentiometer which senses a change of resistance or a position sensing switch which is turned on at that time.

Thus actuated, a signal is sent by sensing mechanism 95 to definition recorder 100 to indicate that hole 40 of worksheet 10 is larger than the diameter of elongated element 82 but less than the diameter of concentric element 84. Thus, definition recorder 100 now has a definition of hole 40. Of course, the definition defined by the FIG. 6B mechanism depends on the number of elements it has, i.e. the greater the number of elements, the finer the definition. The definition thus obtained can then be compared with the prestored data representation of optimal holes, such as that shown in FIG. 3, to correlate the quality of the measured hole with the operational effectiveness of the machine tool.

To elaborate, if hole 40 is made from a partially broken tool that has an original diameter the same size as element 84, and assuming that the hole thus made is not completely free of slivers and concentric, it follows then that probe element 84 is blocked from passing across the plane of worksheet 10. Accordingly, the signal sensed by definition recorder 100 would only indicate that there is a hole made on worksheet 10 that is representative of a hole having a size the same as element 82. Yet at the same time, from the prestored data, it is known that the tool which is effecting the hole, if operating effectively, should make a hole having an opening which matches the diameter of element 84, Thus, by process of elimination, the CNC can determine that there is something amiss with the operation of the machine tool. The same comparison process is of course equally applicable to any machine tool—be it a turret punch, laser cutter or plasma cutter, etc.—as long as the dimension of an optimal or desired hole made by the machine tool has previously been stored in the prestored data memory 48.

Yet another embodiment mechanism of sensor 36 is shown in FIGS. 7A and 7B. For this sensing mechanism, a plurality of elongated elements, each substantially smaller than those shown in FIG. 6b, are aligned and held in a housing 102 attached, as was housing 90 in FIG. 6B, to a portion of frame 4. The plurality of elements 104, represented in the cross-sectional FIG. 7B view as 104a to 104l, are held and aligned by two alignment disks 106 and 108. Disk 108 in turn is made of two wired layers 108a and 108b. Disks 106 and 108 are shown in the plan view in FIG. 7A where each disk has a plurality of holes corresponding to the number of elements 104. In other words, each element 104 is fitted into one of the holes of disk 106 and a corresponding alignment hole in disk 108, and therefore layers 108a and 108b.

Each of elements 104 has at its lower portion thereof a magnetic material 110 of a given polarity. Housing 102 has enclosed at its base portion 102b a magnetized material. Enclosed material 112 may be turned into a magnet having a polarity reverse that of magnetic materials 110 by energizer 114. Once material 112 is energized to have a polarity opposite to that of the magnetic materials 110, elements 104 are repelled by material 112 in the direction of worksheet 10. The repulsion is such that that if there is indeed a hole 40 made in worksheet 10, magnetic materials 110 would pass half way through alignment disk layers 108a and 108b, as indicated at 110a of elements 104e–104i and the dotted portion which protrude pass the top of worksheet 10. As for the remaining elements, since the hole is of such dimension that only elements 104e–104i would pass therethrough, the remaining elements would come into contact with the lower face of worksheet 10. Accordingly, magnetic portions 110 of those elements do not come into the proximity of layers 108a and 108b.

In layers 108a and 108b, with reference to FIG. 7C, each of the holes has connected thereto two wires (as for example 108*al* and 108*bl* for element 104*k*), one over the other, and orthogonal to each other. These wires are energized along different directions. Thus, the only time two wires will be energized at the same time is when the magnetic fields proximate to those wires are disrupted, as for example when the magnetic portion of any one of the elements 104 passes through the hole formed by layers 108*a* and 108*b*.

Since elements 104 are quite small in diameter, the quality of hole 40 can easily be defined, as for example by elements 104*e* to 104*i* at the cross section illustrated in FIG. 7B. Such measured quality is transmitted to the definition recorder 100 by the signal(s) generated by layers 108*a* and 108*b*. Although not clearly shown, the plurality of wires of layer 108*a* extends in a direction going into the paper while the wires of layer 108*b* extend along the direction indicated by arrows 116. Accordingly, when magnetic elements 110 are positioned halfway between layers 108*a* and 108*b*, a pulse is registered only at the location on disk 108 where there is an intersection of wires perpendicular to each other. It is this intersection of wires which causes a pulse to be sent to definition recorder 100.

Thus, by utilizing the mechanism of FIGS. 7A–C, the quality of any holes made by a machine tool on worksheet 10 can be accurately defined. The correlation of the quality of the hole made and the operational effectiveness of the machine tool used to make the hole can of course be correlated as was discussed above.

Another method in which the quality of a hole could be defined is by using a movable probe to touch different points of the opening and recording the coordinates thus probed. A method of utilizing such probed coordinates to define the shape of a hole is disclosed in U.S. Pat. No. 5,016,199 incorporated by reference herein.

Yet another embodiment of the system for defining the quality of any holes made by a machine tool and comparing the same with pre-recorded data in order to determine the operational effectiveness of a machine tool, i.e. whether the tool is broken or partially broken, is illustrated in FIG. 8.

The FIG. 8 embodiment, similar to the embodiment shown in FIG. 3, includes a light source 42 for emitting a light toward the selected portion of worksheet 10 in order to illuminate the same. For the FIG. 8 embodiment, however, instead of using a sensor such as 36 of FIG. 3, an optical image sensor in the form of a camera or a scanner such as a charged coupled device 120 is used. As before, an image is made of the selected portion of worksheet 10 where hole 40 should be. If the recorded image indicates that there is no hole at the selected portion, it is determined that the machine tool is broken. In the case where a punch tool is being evaluated, it is clear that no hole is being punched by that punch tool. In the case where a laser cutter or a plasma cutter is being evaluated, the fact that no hole is formed implies that something is amiss with regard to either the laser beam or the plasma. Of course with such determination, the operation of the machining center is stopped and the machine tool—be it a turret punch, laser or plasma cutter— is at least visually examined to determine whether the machine tool is indeed broken and requires replacement. When the recorded image does contain a hole, such recorded image is compared against the prestored data of an ideal image to evaluate the operational effectiveness, or condition, of the machine tool, per discussion on FIG. 3.

The recording of an image by a camera and the digitizing of the same into an image fed to recorder 44 are conventional and are disclosed for example in U.S. Pat. No. 4,920,273, 4,612,666, 4,463,600 and 4,648,053, all of which disclosures are incorporated by reference herein.

Figure 9:
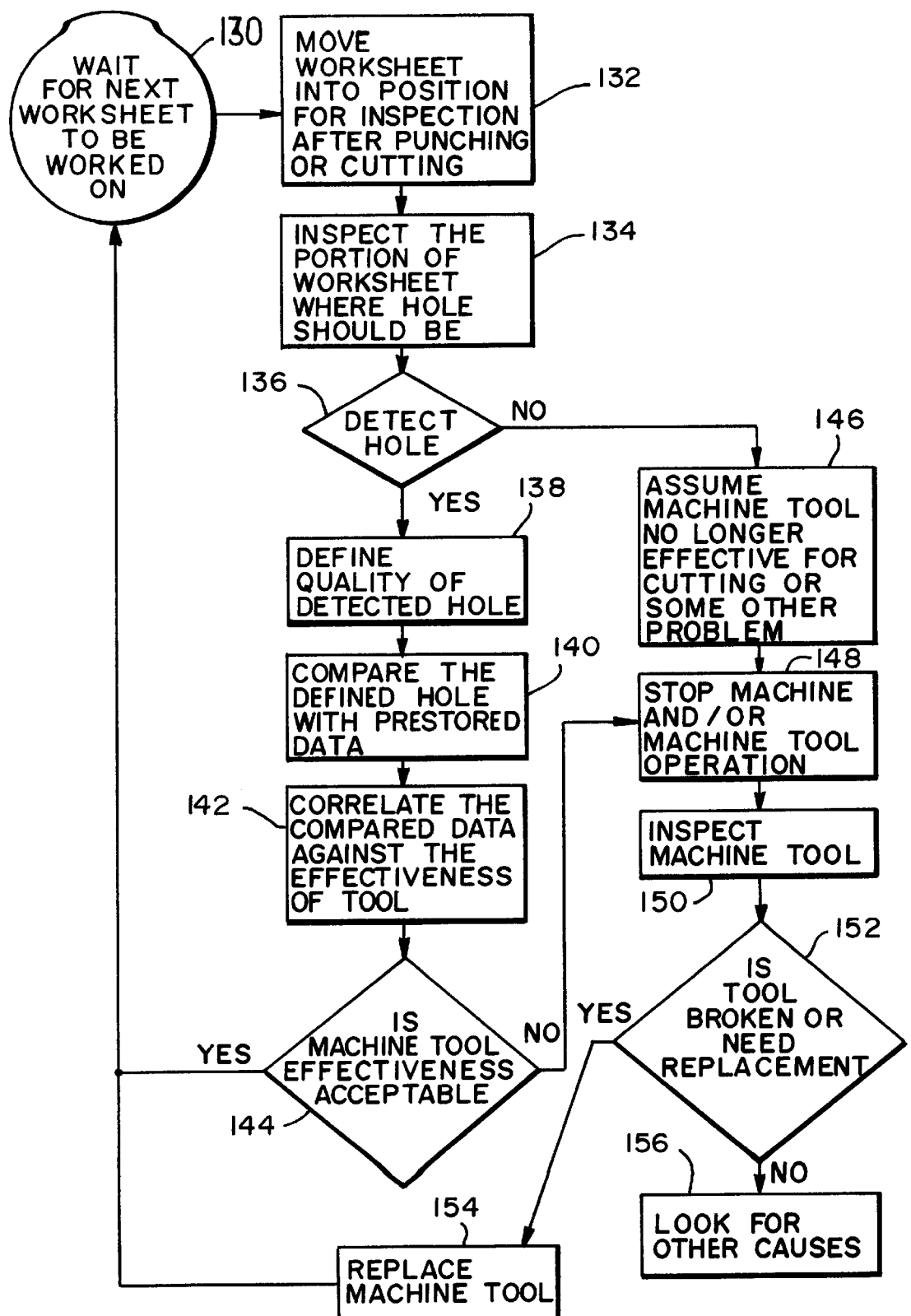
FIG. 9 is a flow chart illustrating the operational steps of the present invention.

Having discussed the various systems and specific detector mechanisms for the present invention system, its operation is discussed herein with reference to the flow chart of FIG. 9.

Starting with circle 130, the system waits for a worksheet to be worked on. Once it has been worked on, the worksheet is moved into position, for example the selected portion thereof where the hole should be is moved from punch station 26 to sensor 36 in block 132. Thereafter, using any one of the above discussed mechanisms, the selected portion of worksheet 10 is inspected at block 134. Whether or not a hole is detected is determined in block 136. If there is indeed a hole detected, then the quality or definition of the hole is defined in block 138 per, for example, the methods disclosed by the various incorporated by reference disclosures.

Thereafter, the defined hole is compared with prestored data that is representative of a desired, or optimal hole at block 140. The thus compared result is used to correlate the quality of the hole or opening made by the machine tool against the operational effectiveness of the machine tool, i.e. whether or not the machine tool is operating effectively, partially broken or broken. This is done in block 142. Whether or not the machine tool is operating at an acceptable operational effectiveness level is determined in block 144. If it is, then the system is returned to circle 130 to await the next to be inspected worksheet. It should be noted that instead of testing for each worksheet, the system can be programmed to only inspect the first few worksheets of a batch of worksheets.

If the machine tool is determined to be operationally ineffective in block 144, the controller of the system would stop the machine and/or the machine tool operation at block 148. Similarly, returning to block 136, if a hole is not detected by any of the above sensing mechanisms in block 136, the processor, or the controller, of the system would assume that the machine tool is broken, or partially broken or that some other problems are causing the machine tool to operate in a non-effective manner. This is done in block 146. With the assumption of block 146, the machine and/or machine tool operation are likewise stopped in block 148.

With the stoppage of the machine and/or machine tool operation, the machine tool is first inspected in block 150. The determination of whether the machine tool is broken or requires replacement is done in decision block 152. If it is determined that replacement is required, such replacement is performed in block 154. Having thus replaced the broken machine tool, the controller would then return to circle 130 and await the next to be inspected worksheet. However, if the machine tool has been determined not to need replacement, then the system would look for other causes in block 156.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope by the appended claims.

I claim:

1. A machining station, comprising:
   a frame;
   a turret rotatably and movably coupled to said frame;
   a worktable positioned relative to said turret and onto which a worksheet is placed;
   at least one tool means mounted to said turret, said tool means effective for making openings on said worksheet;

means positioned proximately to said tool means to detect each successive opening, if any, made by said tool means on said worksheet; and control means for either stopping the operation of said machining station or rotating said turret to replace said tool means with another tool means when said detect means fails to detect any such successive opening on said worksheet.

2. Apparatus of claim 1, wherein said control means comprises:

means for matching the quality of each of said successive opening with prestored data reflecting the quality of an optimal opening, and correlating the result of the match to the effectiveness of said tool means in making openings on worksheets.

3. Apparatus of claim 1, wherein said detect means comprises:

means for emitting at least one electromagnetic wave toward the general area of said worksheet where said opening, if made, is; and means for receiving an echo of said electromagnetic wave reflected from said general area of said worksheet; and wherein said control means comprises:

means for establishing from said echo the quality of each of said successive openings made on said worksheet.

4. Apparatus of claim 1, wherein said detect means comprises:

means for optically recording an image of the portion of said worksheet where said opening should be, said opening, if made, being part of said image; and wherein said control means comprises:

means for comparing said image against a prestored image of a desired opening to determine the effectiveness of said tool means.

5. Apparatus of claim 1, wherein said detect means comprises:

means for collecting the amount of light emanating from the portion of said worksheet where said opening, if made, is; and means for comparing said amount of collected light with a predetermined amount of light representative of said portion of said worksheet including a desired opening to determine the presence and quality of said opening on said worksheet.

6. Apparatus of claim 1, wherein said detect means comprises:

means for probing the location on said worksheet where said opening, if made, is; and wherein said control means comprises:

processor means for deciding said tool means is not operating properly if no opening is sensed, and terminating operation of said tool means accordingly.

7. Apparatus of claim 6, wherein said probing means comprises:

mechanical means including a retractable probe extendable into the plane of said worksheet after said worksheet has been moved into the proper location for detection; and wherein said control means comprises:

processor means for deciding said tool means is effective for making openings on worksheets if said probe is extendable past the plane of said worksheet.

8. Apparatus of claim 7, wherein said retractable probe comprises:

a plurality of extendable elements each activatable, dependent on the amount of extension, to one of at least two states such that said processor means can determine the dimension of said opening made on said worksheet by ascertaining the respective states of said plurality of elements.

9. Apparatus of claim 1, wherein said tool means of said turret comprises at least one additional punch to replace said punch for punching openings on said worksheet.

10. Apparatus of claim 1, wherein said turret further comprises a laser cutter located relative to said tool means for cutting openings on said worksheet.

11. In a sheet machining station having a frame, a worktable whereon a to be worked on worksheet is placed, a tool means positioned relative to said frame for making at least one hole on said worksheet, apparatus for determining whether said tool means is effective for making holes, comprising:

detecting means positioned proximately to said tool means to detect each successive hole, if made, on said worksheet; and control means for correlating the presence or absence of said each successive hole and the quality of said each successive hole, if made, with prestored data immediately after said tool means has supposedly been effected to make a hole to ascertain the operational effectiveness of said tool means.

12. Apparatus of claim 11, wherein said detecting means comprises:

means for probing the location on said worksheet where said hole should be; and wherein said control means comprises:

processor means for deciding said tool means is not operating effectively if no hole is detected or if the quality of the detected hole is determined to be below a predetermined standard, said processor means further causing said tool means to terminate operation as a result.

13. Apparatus of claim 12, wherein said probing means comprises:

mechanical means including a retractable probe extendable into the plane of said worksheet after said worksheet has been moved into the proper location for detection; and wherein if said probe is extendable past the plane of said worksheet, said processor means determines said tool means is effective for making holes.

14. Apparatus of claim 13, wherein said retractable probe comprises:

a plurality of extendable elements each activatable, dependent on the amount of extension, to one of at least two states such that said processor means can determine the dimension of said each successive hole made on said worksheet by ascertaining the respective states of said plurality of elements.

15. Apparatus of claim 11, wherein said detecting means comprises:

means for collecting the amount of light emanating from the portion of said worksheet where said each successive hole, if made, is; and means for comparing said amount of collected light with a predetermined amount of light representative of said portion of said worksheet including a desired opening to determine the presence and quality of said each successive hole on said worksheet.

16. Apparatus of claim 11, wherein said detecting means comprises:

means for emitting at least one electromagnetic wave toward the general area of said worksheet where said each successive hole, if made, is;

said apparatus further including:

means for receiving an echo of said electromagnetic wave reflected from said general area of said worksheet; and means for establishing from said echo the quality of any hole made.

17. Apparatus of claim 11, wherein said detecting means comprises:

optical means for recording an image of the portion of said worksheet onto which said each successive hole should have been, said each successive hole, if made, being a part of said recorded image.

18. Apparatus of claim 17, further comprising:

means for matching the part of said recorded image representative of said each successive hole against a prestored image of an effectively made hole; and processor means for deciding said tool means is operating effectively if said recorded image of said each successive hole substantially matches said prestored image of said effectively made hole.

19. Apparatus of claim 11, wherein said defining means comprises:

means for integrating said detected hole to discriminate the dimension of said hole.

20. Apparatus of claim 11, wherein said sheet machining station comprises a turret punch press and said tool means comprises at least one turret punch.

21. Apparatus of claim 11, wherein said sheet machining station comprises a machine center and said tool means includes a laser cutter.

22. A numerically controlled machining center having at least one work station, a worktable onto which a worksheet for movement with respect to said work station is placed, moving means including gripper means associated with said worktable for presenting at least one selected portion of said worksheet to said work station, tool means positioned proximately to said work station for attempting to effect at least one opening onto said selected portion of said worksheet, comprising:

means positioned proximately to said worktable and said tool means for detecting each successive opening, if made, by said tool means on said selected portion of said worksheet immediately after said tool means has supposedly made an opening on said worksheet;

means working cooperatively with said detecting means for correlating the presence or absence of said each successive opening and, if said opening is present, the quality of said detected opening with prestored data to ascertain the operational effectiveness of said tool means.

23. The center of claim 22, wherein said detecting means comprises:

means for optically recording an image of said selected portion of said worksheet, said each successive opening, if detected, being part of said image; and wherein said correlating means comprises:

means for comparing said image against a prestored image of a desired opening to determine the effectiveness of said tool means.

24. The center of claim 22, wherein said detecting means comprises:

means for collecting the amount of light emanating from said selected portion of said worksheet; and means for comparing said amount of collected light with a predetermined amount of light representative of said selected portion of said worksheet including a desired opening to determine the presence and quality of said each successive opening on said worksheet.

25. The center of claim 22, wherein said detecting means comprises:

means for probing said selected portion of said worksheet for said opening to determine the presence of said opening;

said center further comprising:

controller means for terminating the operation of said tool means if the operational effectiveness ascertained by said correlating means is deemed to be below a given threshold.

26. The center of claim 25, wherein said probing means comprises:

means for emitting at least one electromagnetic wave toward said selected portion of said worksheet where said each successive opening, if effected, is; and means for receiving an echo of said electromagnetic wave reflected from said selected portion of said worksheet; and wherein said detecting means further comprises:

means for establishing from said echo the quality of said each successive opening effected on said worksheet.

27. The center of claim 25, wherein said probing means comprises:

mechanical means including a retractable probe extendable into the plane of said worksheet after said selected portion of said worksheet has been moved into the proper location for detection; and wherein said controller means determines said tool means is effective for making openings on worksheets if said probe is extendable past the plane of said worksheet.

28. The center of claim 27, wherein said retractable probe comprises:

a plurality of extendable elements each activatable, dependent on the amount of extension, to one of at least two states such that said controller means can determine the dimension of said each successive opening made on said worksheet by ascertaining the respective states of said plurality of elements.

29. In a machining work station having at least one worktable onto which a worksheet for movement with respect to said work station is placed, moving means associated with said worktable for presenting at least one selected portion of said worksheet to said work station, tool means positioned proximately to said work station for attempting to effect at least one opening onto said selected portion of said worksheet, a method of ascertaining the operational effectiveness of said tool means, comprising the steps of:

positioning a detection means proximately to said tool means;

detecting the presence of each successive opening, if any, effected by said tool means at said selected portion of said worksheet;

wherein if an opening is immediately detected at said selected portion after said tool means has supposedly made said opening, continuing the operation of said tool means; and wherein if an opening is not immediately detected at said selected portion after said tool means has supposedly made said opening, either stopping the operation of said tool means or replacing said tool means with another tool means.

30. The method of claim 29, wherein said detecting step comprises the step of:

optically recording an image of said selected portion of said worksheet, said each successive opening, if detected, being part of said image; and wherein said method further comprises the step of:
comparing said image against a prestored image of a desired opening to determine the effectiveness of said tool means.

31. The method of claim 29, wherein said detecting step comprises the steps of:

collecting the amount of light emanating from said selected portion of said worksheet; and comparing said amount of collected light with a predetermined amount of light representative of said selected portion of said worksheet including a desired opening to determine the presence and quality of said opening on said worksheet.

32. The method of claim 29, wherein said detecting step comprises the step of:

probing said selected portion of said worksheet to determine the presence of said opening;

said method further comprising the steps of:
defining the quality of any detected opening;
determining said tool means is not operating effectively if no opening is found or if the quality of said detected opening is found to be below a predetermined standard; and terminating the operation of said tool means if said tool means is determined not to operate effectively.

33. The method of claim 32, wherein said probing step comprises the steps of:

emitting at least one electromagnetic wave toward said selected portion of said worksheet where said each successive opening, if effected, is; and receiving an echo of said electromagnetic wave reflected from said selected portion of said worksheet; and said method further comprising the step of:
establishing from said echo the quality of said each successive opening effected on said worksheet.

34. The method of claim 32, wherein said probing step comprises the steps of:

extending a retractable probe into the plane of said worksheet after said selected portion of said worksheet has been moved into the proper location for detection; and wherein said defining step comprises the step of:
determining said tool means is effective for making openings on worksheets if said probe extends past the plane of said worksheet.

35. The method of claim 34, wherein said extending step comprises the step of:

driving a plurality of extendable elements each activatable, dependent on the amount of extension, to one of at least two states to determine the dimension of said opening made on said worksheet by ascertaining the respective states of said plurality of elements.

* * * * *